United States Patent [19]

Weinberg

[11] Patent Number: 4,837,379
[45] Date of Patent: Jun. 6, 1989

[54] FIBRIN-COLLAGEN TISSUE EQUIVALENTS AND METHODS FOR PREPARATION THEREOF

[75] Inventor: Crispin B. Weinberg, Brookline, Mass.

[73] Assignee: Organogenesis Inc., Cambridge, Mass.

[21] Appl. No.: 201,585

[22] Filed: Jun. 2, 1988

[51] Int. Cl.[4] .................... A61K 35/14; A61K 37/12
[52] U.S. Cl. ...................................... 424/101; 514/2; 424/422; 424/423
[58] Field of Search ............................. 514/2; 424/101

[56] References Cited

U.S. PATENT DOCUMENTS

| | | |
|---|---|---|
| 2,533,004 | 12/1950 | Ferry et al. . |
| 4,298,598 | 11/1981 | Schwarz et al. . |
| 4,377,572 | 3/1983 | Schwarz et al. . |
| 4,414,976 | 11/1983 | Schwarz et al. . |
| 4,427,650 | 1/1984 | Stroetmann .................... 424/101 |
| 4,485,096 | 11/1984 | Bell .................................. 424/95 |
| 4,600,574 | 7/1986 | Lindner et al. . |
| 4,627,879 | 12/1986 | Rose et al. .................... 424/101 |

FOREIGN PATENT DOCUMENTS 2102811 7/1982 United Kingdom .

OTHER PUBLICATIONS

Stroetmann—Chem. Abst. vol. 98(1983) p. 149571t.
Stroetmann—Chem. Abst. vol. 100 (1984) p. 39654z.

Primary Examiner—Sam Rosen
Attorney, Agent, or Firm—David G. Conlin; Linda M. Buckley

[57] ABSTRACT

The present invention provides fibrin-collagen tissue equivalents and methods of making and using such tissue equivalents. The present invention also provides methods of forming multi-layer tissue equivalents having improved adherence of the layers. The present invention further provides a method for joining tears in tissue equivalents.

46 Claims, 1 Drawing Sheet

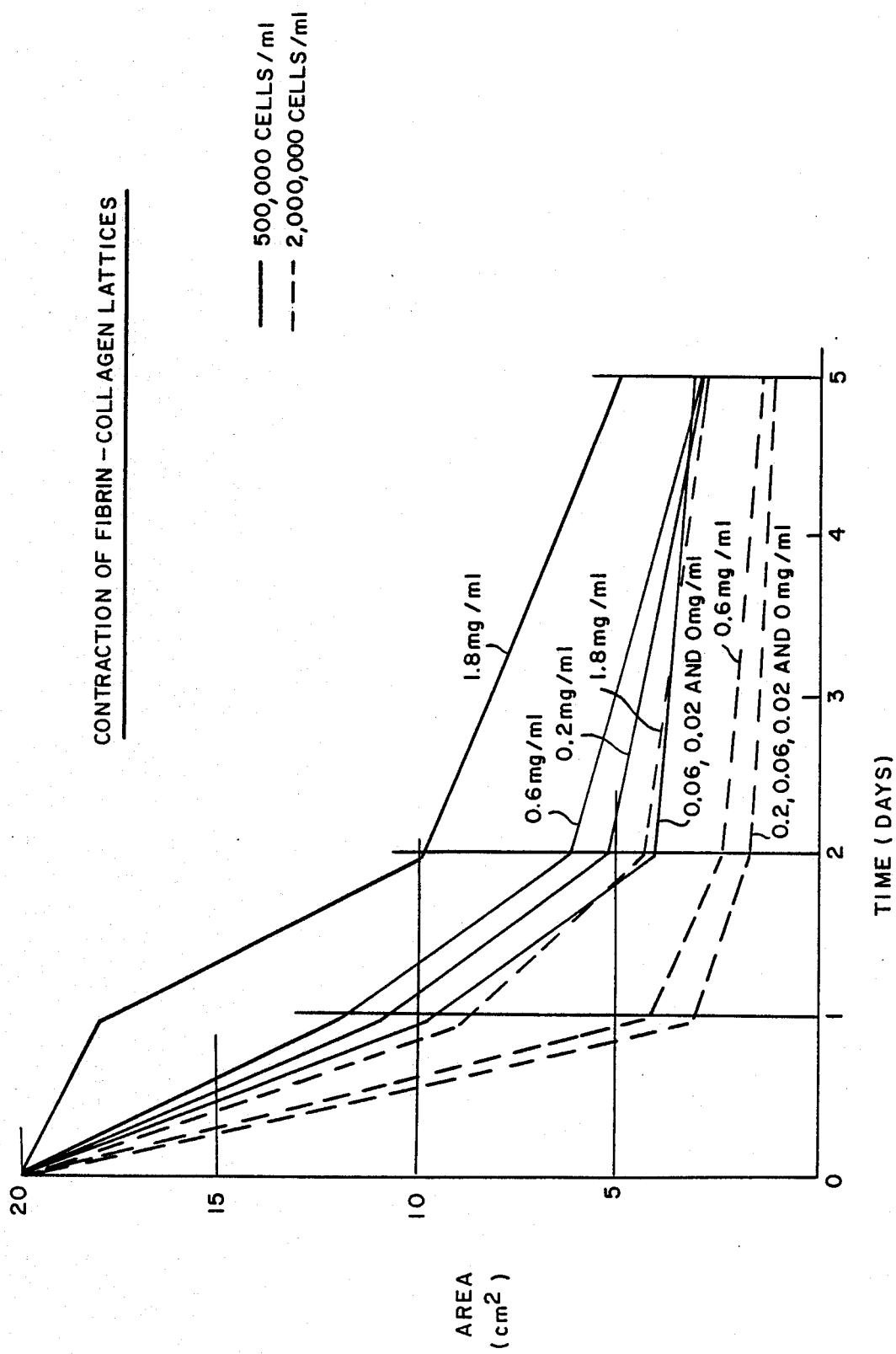

FIBRIN-COLLAGEN TISSUE EQUIVALENTS AND METHODS FOR PREPARATION THEREOF

FIELD OF THE INVENTION

This invention relates to tissue equivalents comprising (i) a hydrated collagen lattice contracted by a contractile agent and (ii) fibrin, and to methods of preparing and using such tissue equivalents. This invention further relates to a method for repair of defects in tissue equivalents.

Tissue equivalents prepared from a hydrated collagen lattice contracted by a contractile agent, such as fibroblast cells or blood platelets to form the tissue equivalent are disclosed in U.S. Pat. Nos. 4,485,096; 4,485,097; 4,539,716; 4,546,500; 4,604,346; and copending U.S. patent application Ser. No. 32,848, filed Mar. 31, 1987, all of which are incorporated herein by reference (hereinafter collectively referred to as "the Patents"). These tissue equivalents include, but are not limited to, equivalents of epithelial tissue, connective tissue, cartilage, bone, blood, organs, glands and blood vessels and comprise living cells and extracellular matrix molecules, principally collagen, and may optionally be provided with components not typically found in normal tissue.

Such tissue equivalents have a broad range of applications including applications in research and development, tissue and organ replacement and testing.

The aforementioned tissue equivalents are populated with cells that can remain alive for long periods of time and can be produced in quantity with the assurance that the units produced will be essentially uniform. Cells in such tissue equivalents resemble cells of normal tissue in their structural arrangement, in their biosynthetic output, and in their permeability. It should be understood that these tissue equivalents need not be human but may be those of any animal as desired.

Human skin tissue equivalents permit the growth of normal human epidermal cells that differentiate fully producing a normal stratum corneum and a complete basal lamina which have not, to date, been obtained by routine culture methods. Such skin tissue equivalents have been extensively used as a permanent skin replacement in animal experiments and are currently undergoing clinical testing in the United States. The morphological appearance of such skin tissue equivalents is normal, its constituent cells persist after grafting as shown by genetic marking, and its functional performance has been demonstrated. See, e.g., *Science*, 211: 1052–1054 (1981); *J. Invest. Dermatol.* 81: 2s–10s (1983).

Skin tissue equivalent fabricated in vitro bears a close resemblance to natural skin. It consists of a multilayered epidermis with well-developed basal cells joined to the dermal layer by a fully structured basal lamina. The dermal layer comprises a collagen matrix in which dermal fibroblasts are distributed. Cells in the three-dimensional collagen matrix achieve a state of differentiation in many respects similar to that which prevails in vivo. For example, resident fibroblasts are synthetically active and enrich the matrix in vitro both with collagen, and a number of other molecular species, and exhibit permeability properties typical of a cell in vivo. See, e.g., *Collagen Rel. Res.* 4: 351–364 (1984). The effects of steroids on the capacity of human and rat fibroblasts to contract tissue equivalent lattices has been evaluated. See *J. Invest. Dermatol.* 82: 341–344 (1984). A skin tissue equivalent model has been used to fabricate tissues with psoriatic and normal cells for the study of the disease psoriasis (*Science*, 230: 669–672, 1985). Recently it has been shown that skin tissue equivalents can be pigmented by inclusion of melanocytes that donate pigment to keratinocytes and that the process is speeded up in vitro by ultraviolet radiation (*J. Invest. Dermatol.* 87: 642–647, 1986).

Human blood vessel tissue equivalents are typically multilayered tubes constructed from extracellula matrix molecules and cultured vascular cells. See, e.g., *Science* 231: 397–400, 1986; U.S. Pat. Nos. 4,539,716 and 4,456,500. They resemble human blood vessels in structure and function. Blood vessel tissue equivalents may be provided with a lining of a monolayer of endothelial cells which produce a basal lamina in vitro. Together, the endothelial cells and basal lamina constitute the intima of such blood vessel tissue equivalents. The middle layer consists of smooth muscle cells in a collagen lattice, and constitutes the media of such blood vessel tissue equivalents. The smooth muscle cells contribute collagen, elastin, and other molecules to the matrix. In some embodiments, other extracellular matrix components such as hyaluronic acid are optionally added for particular applications. The outer layer of the blood vessel tissue equivalent is fabricated from adventitial fibroblasts in a collagen lattice an constitutes the adventitia of the blood vessel tissue equivalent. A support member, e.g., a synthetic mesh, may also be optionally included in the blood vessel tissue equivalent, typically in the wall between the media and adventitia, to strengthen the blood vessel tissue equivalent. A removable, protective impermeable member, e.g., a plastic sleeve adjacent the abluminal surface may also be optionally provided.

It should be understood that the order of the layers in such blood vessel tissue equivalents may be organized in the reverse order of that typically found in a natural blood vessel. For example the endothelial cells and basal lamina which constitute the intima of normal blood vessels can be located so that they are on the outside of a tubular blood vessel tissue equivalent. The middle layer of such a blood vessel tissue equivalent consists of smooth muscle cells and a collagen lattice, thereby constituting the media of the blood vessel tissue equivalent. The inner layer of such a reverse order blood vessel tissue equivalent is fabricated from adventitial fibroblasts in a collagen lattice and forms the layer that would constitute the adventitia of a normal blood vessel.

Blood vessel tissue equivalents can be made for different types of blood vessels by using cells cultured from the appropriate sources. For example, arterial blood vessel tissue equivalents further comprise cells cultured from the corresponding layers of an artery; capillary blood vessel tissue equivalents further comprise capillary endothelial cells and pericytes in place of the adventitial fibroblasts; and venous blood vessel tissue equivalents further comprise cells cultured from veins and are fabricated with thinner outer layers than arterial blood vessel tissue equivalents. For the studies of certain diseases, cells cultured from patients with the particular disease are incorporated into the blood vessel tissue equivalent.

Tissue equivalents can be cast in any desired shape. Skin tissue equivalents are generally cast as a flat sheet and blood vessel equivalents are generally fabricated as a hollow tube or a network of hollow tubes. However, it may be desirable to change the natural geometry or configuration of the tissue equivalent. For example, skin tissue equivalent may be cast as a cylinder rather than as a sheet and the layers of blood vessel tissue equivalent may be cast in the reverse of the order of natural blood vessels as described above.

It has been discovered through the use of the aforementioned tissue equivalents that for some applications it is desirable to strengthen the collagen lattice itself, and where the tissue equivalent is formed of layers, to strengthen the joining of the layers themselves. In applications which involve substantial mechanical handling of the tissue equivalent, such as extensive suturing and cutting, it is especially desirable to strengthen the collagen lattice. By way of example, blood vessel tissue equivalents comprise multiple layers of collagen lattices, and it has been discovered that in some instances these layers may delaminate under mechanical stresses such as pressure, cutting, or suturing. Furthermore, because the blood vessel tissue equivalent is for some applications cut and sewn in place for use as a vascular prosthesis, it must withstand inter-vascular pressures immediately (as soon as the clamps are removed from the recipient's vessels), and the blood vessel equivalent doesn't have the opportunity for the in vivo strengthening that, for example, the living skin equivalent has.

Thus, ways of strengthening such tissue equivalents are desired for certain applications.

BRIEF DESCRIPTION OF THE DRAWINGS

FIG. 1. is a plot of data illustrating the contraction of fibrin-collagen lattices having differing fibrinogen and fibroblast cell concentrations.

SUMMARY OF THE INVENTION

The present invention discloses tissue equivalents comprising (i) a hydrated collagen lattice contracted by a contractile agent and (ii) fibrin, and methods of making such tissue equivalents. The present invention also discloses methods for repair of defects in tissue equivalents. The tissue equivalents of the present invention offer advantages over those disclosed in the Patents in terms of greater strength and, in the case of multi-layered tissue equivalents, both greater strength and adhesion between layers.

Fibrin may be incorporated in or added to the collagen lattice either during or after formation thereof. In some embodiments of the present invention, fibrin may be incorporated in the layers during formation thereof or in the formed layers or both. Furthermore, improved adherence of the layers of multi-layer collagen or fibrin-collagen tissue equivalents may be achieved by application of fibrinogen and thrombin to the surface of one or more of the layers to be joined.

The concentration of fibrin and collagen, respectively, in the tissue equivalents of the present invention is from about 3 to about 30 mg/cm$^3$, more preferably the fibrin is at a concentration from about 15 to about 25 mg/cm$^3$ and the collagen is at a concentration of from about 10 to about 15 mg/cm$^3$. In embodiments wherein fibrinogen and thrombin are applied to the surface of a collagen or fibrin-collagen tissue equivalent, the concentration of fibrin will typically form a gradient, the highest concentration being at or near the surface of the tissue equivalent to which the fibrinogen and thrombin are applied.

Preferred contractile agents for use in the present invention include fibroblast cells, smooth muscle cells, striated muscle cells, heart muscle cells or blood platelets.

The tissue equivalents of the present invention may further include an agent which can cross-link fibrin and collagen, e.g., Factor XIII, to provide tissue equivalents of even greater enhance strength and stability. Other optional additives include agents which protect the fibrin-collagen lattice from degradation, e.g., protease inhibitors.

The fibrin-collagen tissue equivalents of the present invention may also include living cells such as keratinocytes or other epithelial cells or other tissue cells and other additives such as demineralized bone powder gylcosoaminoglycans, e.g., hyaluronic acid, other connective tissue proteins, e.g., fibronectin or elastin and other factors, e.g., growth factors or angiogenic factors.

Methods in accordance with the present invention include methods for (i) making fibrin-collagen tissue equivalents, (ii) improving the adherence of the layers of multi-layered collagen or fibrin-collagen tissue equivalents, and (iii) repairing defects, e.g., a tear in tissue equivalents.

One method in accordance with the present invention whereby a fibrin-collagen tissue equivalent is formed comprises:

(a) forming a mixture comprising collagen, fibrinogen, an agent which causes the formation of fibrin from fibrinogen and at least one contractile agent under conditions to form a gel having the collagen, fibrinogen, the agent which causes the formation of fibrin from fibrinogen and the contractile agent dispersed within said gel mixture; and (b) maintaining the gel prepared in step (a) under conditions which permit contraction of the gel to form a tissue equivalent.

In such mixtures the collagen and the fibrinogen are each at a concentration of from about 0.3 to about 3.0 mg/ml. More preferably, the collagen is at a concentration of from about 1.0 to 1 5 mg/ml, the fibrinogen is at a concentration of from about 1.5 to about 2.5 mg/ml, and thrombin is at a concentration of from about 0.1 to about 10 units/ml.

Another method of the present invention for producing a fibrin-collagen tissue equivalent comprises:

(a) forming a mixture comprising collagen and at least one contractile agent under conditions to form a gel having the collagen and contractile agent dispersed therein;

(b) maintaining the gel obtained in step (a) under conditions which permit contraction of the gel to form a tissue equivalent; and (c) applying fibrinogen and an agent which causes the formation of fibrin from fibrinogen to at least one surface of the tissue equivalent of step (b).

The agent which causes the formation of fibrin from fibrinogen preferably comprises thrombin. In step (c) the fibrinogen and thrombin are preferably applied in solution. In such embodiments, the fibrinogen solution is typically at a concentration of from about 5 mg/ml to about 25 mg/ml and the thrombin solution is at a concentration of from about 25 to about 500 units/ml. The method of applying fibrinogen and thrombin to the surface of a tissue equivalent may also be used to provide greater adhesion between the layers of multi-layer collagen or fibrin-collagen tissue equivalents.

The present invention also provides a method of producing a tissue equivalent having at least two layers the method comprising:

(a) forming a mixture comprising collagen, at least one contractile agent, fibrinogen and an agent which causes the formation of fibrin from fibrinogen under conditions to form a gel having the collagen, contractile agent, fibrinogen and agent which causes the formation of fibrin from fibrinogen dispersed within the gel and maintaining the gel under conditions which permit contraction of the gel to form a first tissue equivalent;

(b) applying a mixture comprising fibrinogen and an agent which causes the formation of fibrin from fibrinogen to the first tissue equivalent; and (c) contacting a second tissue equivalent produced in accordance with step (a) above with the first tissue equivalent; and (d) repeating steps (b) and (c) if additional layers of tissue equivalents are desired.

The present invention further provides a method of repairing a defect in a tissue equivalent comprising a hydrated collagen lattice contracted by a contractile agent or (i) a hydrated collagen lattice contracted by a contractile agent and (ii) fibrin, e.g., joining a tear, the method comprising:

(a) applying a mixture comprising fibrinogen and an agent which causes the formation of fibrin from fibrinogen to the defect in the tissue equivalent; and (b) maintaining the tissue equivalent of step (a) under conditions to permit formation of fibrin.

DETAILED DESCRIPTION OF THE INVENTION

Tissue equivalents prepared from a hydrated collagen lattice contracted by a contractile agent to form the tissue equivalent are disclosed in the Patents. It has been unexpectedly discovered that by incorporating fibrin in the collagen lattice of such tissue equivalents, tissue eqivalents having improved properties are produced. Thus, the tissue equivalents of the present invention, although similar, in both methods of preparation and use, to those comprising a hydrated collagen lattice as disclosed in the Patents, further comprise fibrin, resulting in tissue equivalents having greater strength and, in the case of multi-layered tissue equivalents, greater adhesion between the layers.

Tissue equivalents of the present invention are prepared as described in the Patents, except that in accordance with the present invention, fibrin is additionally incorporated in or added to the hydrated collagen lattice, either during and/or after formation thereof. Materials used to prepare the tissue equivalents of the present invention may include collagen; fibrinogen; an agent, such as thrombin, which causes the formation of fibrin from fibrinogen; an agent, such as Factor XIII, which causes the fibrinogen and collagen to cross-link; one or more contractile agents; living cells; nutrient media; and additives.

A convenient technique for incorporating fibrin in the tissue equivalents of the present invention during formation thereof, involves rapidly mixing together an acidic solution of collagen having a pH of from about 3 to about 4, preferably about 3.5, and a solution of fibrinogen and thrombin with nutrient media containing fibroblast cells, adjusting the pH of the resultant solution, if necessary, to from about pH 6.6 to about pH 7.8, transferring the resultant solution (the "casting mixture") into an appropriate mold or casting device and incubating it at a temperature preferably from about 35° to about 40° C. It is most convenient to adjust pH and combine the ingredients of the casting mixture simultaneously. However, these steps may be carried out in any desired order, provided that the steps are completed so that the casting mixture can be transferred to a mold for appropriate setting. The collagen fibrils precipitate from the casting mixture as a result of warming the solution and raising the pH; the fibrinogen, catalyzed by thrombin, forms fibrin; the fibrin clots in the presence of the calcium ions; and the fibrin clot and collagen gel intertwine, forming a hydrated collagen lattice containing fibrin and contracted by a contractile agent.

When appropriate concentrations of fibrinogen and collagen are used in the casting mixture, the resulting fibrin-collagen lattice is stronger and tougher than either fibrin clots or lattices made with collagen alone. Desirable concentrations of collagen and fibrinogen in the casting mixture include from about 0.3 to about 3.0 mg/ml collagen and from about 0.3 to about 3.0 mg/ml fibrinogen. Particularly preferred concentrations ar from about 1.0 to about 1.5 mg/ml collagen and from about 1.5 to about 2.5 mg/ml fibrinogen.

The final concentration of collagen and fibrin in the fibrin-collagen tissue equivalents of the present invention is about 10 times higher than in the casting mixture. Fibrin and collagen are each at a concentration of from about 3 to about 30 mg/cm$^3$ in the tissue equivalents of the present invention. More preferably the fibrin is at a concentration from about 15 to about 25 mg/cm$^3$ and the collagen is from about 10 to about 15 mg/cm$^3$.

A higher density of contractile agent than is described in the Patents to contract a collagen lattice is often required to contract a fibrin-collagen lattice. For example, a collagen lattice made using fibroblast cells in suspension at 500,000 cells/ml contracted at the same rate as a fibrin-collagen lattice made with fibrinogen at 1.8 mg/ml and with fibroblast cells at 2,000,000 cells/ml (FIG. 1.).

Although it is usually preferable to prepare the fibrin-collagen tissue equivalents of the present invention by casting the collagen and fibrin lattices together, fibrin may be incorporated in the collagen lattice after the lattice is formed by applying fibrinogen and thrombin to the surface of the collagen lattice. In one embodiment of the present invention, a tissue equivalent is formed as described in the Patents, a fibrinogen solution is then applied and allowed to diffuse into the collagen lattice, and after the fibrinogen had diffused into the collagen lattice, a thrombin solution, optionally containing Factor XIII, is applied to the lattice. Although it is most convenient to apply the fibrinogen and thrombin sequentially as described above, it is not necessary to do so. When fibrinogen and thrombin are applied to the surface of a formed collagen or fibrin-collagen lattice, desirable concentrations of fibrinogen and thrombin range from about 10 to about 50 mg/ml and from about 10 to about 500 units/ml, respectively.

Any agent which causes the formation of fibrin from fibrinogen and which is compatible with the other ingredients in the casting mixture may be used in the practice of the present invention. At present, thrombin is the only such agent known to those skilled in the art. Calcium ions are necessary for the formation of fibrin from fibrinogen in the presence of thrombin and are conveniently provided in the nutrient medium. However, calcium ions can be otherwise provided to the casting mixture as desired. Desired concentrations of thrombin in the casting mixture range from about 0.1 to about 10.0 units/ml. When thrombin is applied to the surface of a formed collagen or fibrin-collagen lattice, it is preferable to use a concentrated solution of thrombin of about 25 units/ml.

The strength and stability of tissue equivalents in accordance with the present invention can be further enhanced, if desired, by the use of an agent such as Factor XIII (Fibrin Stabilizing Factor), which can cross link fibrin and collagen. Factor XIII is used in an amount to achieve the desired degree of cross-linking, for example 0.1 to about 5 units/ml. Other agents which can cross-link fibrin and collagen or chemically stabilize the fibrin-collagen lattice may also be used. In some instances, it may be desirable to include one or more protease inhibitors in the tissue equivalents of the present invention in order to make the fibrin-collagen lattice less susceptible to proteolytic degradation.

Collagen lattices may be cast in successive layers to form multilayer tissue equivalents. See U.S. Pat. Nos. 4,539,716 and 4,546,500. It has been found that adherence of the layers of such tissue equivalents is improved by incorporation of fibrin in the collagen lattice as described above. Furthermore, adherence of the layers of multi-layer collagen or fibrin-collagen tissue equivalent may be improved by the application of fibrinogen and thrombin to the surface of one or both of the layers of formed collagen or fibrin-collagen lattices which are to be joined to form the multilayer tissue equivalents.

Tissue equivalents of the present invention can be prepared in both serum-free media and media containing serum. Preparation in serum-free media is more economical and also eliminates the presence of unidentified factors usually present in the plasma, thus, providing better process control.

The invention will be further understood with reference to the following examples, which are purely exemplary in nature, and are not meant to be utilized to limit the scope of the invention.

Materials used in the following examples were obtained from the sources indicated in the examples or made in accordance with the indicated publications.

EXAMPLE 1

Preparation of Tissue Equivalents Cast with Fibrinogen

Fibrinogen (Miles Laboratories) was dissolved in 1.76× concentrated McCoy's 5A culture medium to give nominal concentrations of 10, 3, 1, 0.3, and 0.1 mg/ml. Fibrin-collagen lattices were made by mixing together 2.3 ml concentrated medium, 0.45 ml fetal bovine serum (FBS), 0.25 ml 0.1 N NaOH, 1.5 ml rat tail tendon collagen dissolved at 3 mg/ml in 0.1% acetic acid and 0.5 ml of fibroblasts suspended in McCoy's 5A supplemented with 10% FBS and 5 units of thrombin (Sigma Chemical Co.). The fibroblasts were used at densities of either 500,000 cells/ml or 2,000,000 cells/ml. Control lattices were made as above but using medium with no added fibrinogen.

The resulting mixtures were poured into individual 60 mm plastic Petri dishes and incubated at 37° C. in a humidified, 5% $CO_2$–95% air atmosphere. The diameters of the fibrin-collagen lattices were measured on subsequent days and the results are shown in FIG. 1. As the concentration of fibrinogen was increased, more cells were required to contract the lattice. Lattices made with the tw highest concentrations of fibrinogen appeared more opaque and felt less gelatinous than lattices in which collagen was the only or predominant extracellular matrix component. Since the fibrinogen preparation used consisted of 60% clottable protein and only approximately two-thirds of it went into solution, the actual concentrations of fibrinogen in the casting mixtures were approximately 1.8, 0.6, 0.2, 0.06 and 0.02 mg/ml respectively.

A general description of procedures and reagents may also be found in the Patents, with the exception of procedures and reagents relating to fibrinogen and fibrin.

EXAMPLE 2

Preparation of Tissue Equivalents with Incorporation of Fibrin in Collaqen Lattice After Formation Thereof Two collagen lattices were prepared as in Example 1 above, but without any fibrinogen or thrombin, and allowed to contract for several days. They were rinsed in serum-free medium several times to remove serum and then excess medium was aspirated. Drops of a concentrated (25 mg/ml) aqueous solution of fibrinogen were placed on the surface of each lattice and allowed to diffuse into the lattice. Drops of thrombin (500U/ml) and fibrin stabilizing factor (Factor XIIIa, 10 U/ml, Calbiochem) were applied to one lattice, the second lattice was then placed on the first and held with gentle pressure for about one minute. Culture medium containing serum was added to cover the lattices. After one hour each lattice was grabbed with a pair of forceps but they could not be pulled apart. The bond was sufficiently strong that the lattices themselves tore before separating. Control lattices treated similarly except without fibrinogen added simply floated apart. Thus, fibrinogen added to the lattices after they are cast and contracted can be used to join them. This method is also used to join the edges of tissue equivalents or to repair a tear or cut in a tissue equivalent.

EXAMPLE 3

Preparation of Blood Vessel Tissue Equivalents Cast with Fibrinogen

Blood vessel tissue equivalents were cast in heparinized 25 mm cylinders with 6mm central mandrels, 13.8 ml 1.76× McCoy's 5A medium containing fibrinogen at nominal concentrations of 0, 5.5, or 11 mg/ml, 9.0 ml rat tail tendon collagen (3.3 mg/ml in 0.1% acetic acid), 2.7ml FBS (selected for coagulant activity equivalent to at least 1 U/ml of thrombin), 1.5 ml 0.1 N NaOH, and 3.0 ml of a suspension of vascular smooth muscles in McCoy's 5A medium supplemented with 10% FBS. Smooth muscle cells were used at densities of 500,000 cells/ml or 2,000,000 cells/ml. After the smooth muscle layer had contracted around the mandrel a Dacron® mesh was slipped over the first layer, and a second layer cast around it using adventitial fibroblasts rather than smooth muscle cells. Two weeks after casting the second layer, the blood vessel tissue equivalents were removed form the mandrel and their burst strengths were measured as described in *Science* 231: 397–400 (1986).

Blood vessel tissue equivalents made without fibrinogen in accordance with the Patents had burst strengths between 100 and 120 mm Hg. During the burst strength tests, their inner (smooth muscle) and outer (adventitial fibroblast) layers separated.

Blood vessel tissue equivalents made using a nominal concentration of 5.5 mg/ml fibrinogen in the concentrated medium (actual concentration in casting mixture of approximately 1 mg/ml) had burst strengths between 135 and 150 mm Hg. The layers could be easily pulled apart with forceps and separated if the blood vessel tissue equivalent was cut across with surgical scissors.

Blood vessel tissue equivalents made with a nominal concentration of 11 mg/ml fibrinogen in the concentrated medium (approximately 2.0 mg/ml in the final casting mixture) had burst strengths in the range 165–180 mm Hg. They did not delaminate during pressure testing nor when cut either transversely or obliquely. The cut pieces could be sutured together without delaminating. A 6-0 polypropylene suture (Davis & Geck) with a tapered needle was used for this test.

Thus, the layers of blood vessel tissue equivalents made with fibrin-collagen lattices allow greater ease of handling by conventional surgical techniques as well as having increased burst strenths over blood vessel tissue equivalents made with collagen lattices in accordance with the Patents.

EXAMPLE 4

Preparation of Blood Vessel Tissue Equivalents Cast with Fibrinogen in Serum Free Media Blood vessel tissue equivalents were cast in heparinized glass cylinders (25 mm diameter) with 6 mm central mandrels. To make a 5 cm length of blood vessel tissue equivalent, a final casting volume of 20 ml was used.

Bovine fibrinogen (Miles Laboratories) was dissolved in 1.7× concentrated DMEM:Ham's F12 medium with high glucose (MA Bioproducts) at a concentration of (nominally) 10.2 mg/ml. This was supplemented with glutamine (MA Bioproducts), gentamycin (MA Bioproducts), sodium bicarbonate, and 11% (by volume) of 0.05 N sodium hydroxide. A quantity sufficient for 51% of the casting volume was prepared.

This mixture was added to Type I collagen (from porcine skin) dissolved at 3 mg/ml in 0.05% acetic acid. The volume of collagen solution was 30% of the final volume.

Smooth muscle cells, suspended at 1.5–2.0 cells/ml in 1× DMEM:Ham's F12 were added to 10% of the final volume.

A growth supplement (Scott Laboratories and Sigma Chemical Co.) containing insulin, transferrin, selenium, triiodothyronine, steriods, ethanolamine and o-phosphorylethanolamine, thrombin, and epidermal growth factor was added as a volume equal to 9% of the final volume.

This mixture was poured into the mold and incubated at 37° in a 5% $CO_2$ atmosphere.

A mesh was applied after 1 week.

A second layer was applied as above except using adventitial fibroblasts rather than smooth muscle cells.

After an additional week these were removed from the mandrel and cut with a surgical scissors to demonstrate the adhesion between the medial and adventitial layers. The medial and adventitial layers of control blood vessel tissue equivalents made with collagen lattices were more prone to separation upon cutting than were the layers of blood vessel tissue equivalents made with fibrin-collagen lattices. Thus, fibrin-collagen lattices can be made in serum free medium and continue to provide improved adhesion and handling properties over those made with collagen alone.

It is understood that the examples and embodiments described herein are for illustrative purposes only, and that various modifications or changes in light thereof that will be suggested to persons skilled in the art are to be included in the spirit and purview of this application and the scope of the approved claims.

What is claimed is:

1. A tissue equivalent comprising (i) a hydrated collagen lattice contracted by a contractile agent and (ii) fibrin.

2. The tissue equivalent of claim 1, wherein the fibrin and the collagen are cross-linked.

3. The tissue equivalent of claim 1, wherein the collagen and the fibrin are each at a concentration of from about 3 to 30 mg/cm$^3$.

4. The tissue equivalent of claim 1, wherein the collagen is at a concentration of from about 10 to about 15 mg/cm$^3$ and the fibrin is at a concentration of from about 15 to about 25 mg/cm$^3$.

5. The tissue equivalent of claim 1, wherein the contractile agent comprises a cell type which is capable of contracting a hydrated collagen lattice.

6. The tissue equivalent of claim 1, wherein the contractile agent comprises fibroblasts, smooth muscle cells, striated muscle cells, heart muscle cells or blood platelets.

7. The tissue equivalent of claim 1, wherein the lattice further comprises keratinocytes or demineralized bone powder.

8. The tissue equivalent of claim 1, wherein the tissue equivalent is a skin, bone, blood vessel, organ or gland tissue equivalent.

9. The tissue equivalent of claim 1, further comprising at least one protease inhibitor.

10. A tissue equivalent having at least two layers, wherein one or more of the layers comprises (i) a hydrated collagen lattice contracted by a contractile agent and (ii) fibrin.

11. A method of producing a tissue-equivalent, the method comprising:
    (a) forming a mixture comprising collagen, fibrinogen, an agent which causes the formation of fibrin from fibrinogen and at least one contractile agent under conditions to form a gel having the collagen, the fibrinogen, the agent which causes the formation of fibrin from fibrinogen and the contractile agent dispersed within said gel mixture; and
    (b) maintaining the gel prepared in step (a) under conditions which permit contraction of the gel to form a tissue equivalent.

12. The method of claim 11, wherein the agent which causes the formation of fibrin from fibrinogen comprises thrombin.

13. The method of claim 11, wherein the mixture further comprises an agent or is exposed to an agent which causes the cross-linking of fibrin and collagen.

14. The method of claim 13, wherein the cross-linking agent is Factor XIII.

15. The method of claim 11, additionally including adding living cells into or onto the tissue equivalent.

16. The method of claim 11, wherein the collagen and the fibrinogen are each at a concentration of from about 0.3 to about 3.0 mg/ml.

17. The method of claim 11, wherein the collagen is at a concentration of from about 1.0 to 1.5 mg/ml and the fibrinogen is at a concentration of from about 1.5 to about 2.5 mg/ml.

18. A tissue equivalent formed according to the method of claim 11.

19. The tissue equivalent of claim 18, wherein the collagen and the fibrin are each at a concentration of from about 3 to about 30 mg/cm$^3$.

20. The tissue equivalent of claim 18, wherein the collagen is at a concentration of from about 10 to about 15 mg/cm$^3$ and the fibrin is at a concentration of from about 15 to about 25 mg/cm$^3$.

21. A method of producing a tissue equivalent, the method comprising:
   (a) forming a mixture comprising collagen and at least one contractile agent under conditions to form a gel having the collagen and contractile agent dispersed therein;
   (b) maintaining the gel obtained in step (a) under conditions which permit contraction of the gel to form a tissue equivalent; and
   (c) applying fibrinogen and an agent which causes the formation of fibrin from fibrinogen to at least one surface of the tissue equivalent of step (b).

22. The method of claim 21, wherein the agent which causes the formation of fibrin from fibrinogen comprises thrombin.

23. The method of claim 21, wherein the mixture further comprises an agent or is exposed to an agent which causes the cross-linking of fibrin and collagen.

24. The method of claim 23, wherein the cross-linking agent comprises Factor XIII.

25. The method of claim 21, additionally including adding living cells into or onto the tissue equivalent.

26. The method of claim 21, wherein the collagen and the fibrinogen are each at a concentration of from about 0.3 to about 3.0 mg/ml.

27. The method of claim 21, wherein the collagen is at a concentration of from about 1.0 to about 1.5 mg/ml and the fibrinogen is at a concentration of from about 1.5 to about 2.5 mg/ml.

28. A tissue equivalent formed according to the method of claim 21.

29. The tissue equivalent of claim 28, wherein the collagen and the fibrin are each at a concentration of from about 3.0 to about 30.0 mg/cm$^3$.

30. The tissue equivalent of claim 28, wherein the collagen is at a concentration of from about 10.0 to about 15.0 mg/cm$^3$ and the fibrin is at a concentration of from about 15.0 to about 25.0 mg/cm$^3$.

31. A method of producing a tissue equivalent having at least two layers, the method comprising:
   (a) forming a mixture comprising collagen and at least one contractile agent under conditions to form a gel having the collagen and contractile agent dispersed within the gel and maintaining the gel under conditions which permit contraction of the gel to form a first tissue equivalent;
   (b) applying a mixture comprising fibrinogen and thrombin to the first tissue equivalent; and
   (c) contacting a second tissue equivalent produced in accordance with step (a) above with the first tissue equivalent; and
   (d) repeating steps (b) and (c) if additional layers of tissue equivalents are desired.

32. The method of claim 31, wherein the mixture of step (a), step (c) or steps (a) and (c) further comprises fibrinogen and thrombin.

33. A method in accordance with claim 31, wherein a mixture comprising fibrinogen and thrombin is applied to the surface of the tissue equivalent of step (c).

34. A method of producing a tissue equivalent having at least two layers, the method comprising:
   (a) forming a mixture comprising collagen, at least one contractile agent, fibrinogen and an agent which causes the formation of fibrin from fibrinogen under conditions to form a gel having the collagen, contractile agent, fibrinogen and the agent which causes the formation of fibrin from fibrinogen dispersed within the gel and maintaining the gel under conditions which permit contraction of the gel to form a first tissue equivalent;
   (b) applying a mixture comprising fibrinogen and an agent which causes the formation of fibrin from fibrinogen to the first tissue equivalent; and
   (c) contacting a second tissue equivalent produced in accordance with step (a) above with the first tissue equivalent; and
   (d) repeating steps (b) and (c) if additional layers of tissue equivalents are desired.

35. A method of preparing a tissue-equivalent, comprising:
   (a) forming a acidic solution of collagen;
   (b) combining fibrinogen, an agent which causes the formation of fibrin from fibrinogen, at least one contractile agent and nutrient medium with the acidic solution of collagen;
   (c) raising the pH and the temperature of the solution of collagen to a level sufficient to cause the collagen to gel and form a hydrated collagen lattice containing the fibrinogen, the agent which causes the formation of fibrin from fibrinogen, and the contractile agent; and
   (d) maintaining the lattice, fibrinogen, the agent which causes the formation of fibrin from fibrinogen, and the contractile agent under conditions sufficient for the agent to cleave fibrinogen to form fibrin and the contractile agent to contract the collagen lattice thereby forming a tissue equivalent.

36. The method of claim 35 wherein steps (b) and (c) are done simultaneously.

37. The method of claim 35, wherein the mixture further comprises an agent which causes the cross-linking of fibrinogen and collagen.

38. The method of claim 36, wherein the agent is Factor XIII.

39. The method of claim 35, additionally including adding living cells into or onto the tissue equivalent.

40. The method of claim 35 wherein the collagen and the fibrinogen are each at a concentration of from about 0.3 to about 3.0 mg/ml.

41. The method of claim 35, wherein the collagen is at a concentration of from about 1.0 to about 1.5 mg/ml and the fibrinogen is at a concentration of from about 1.5 to about 2.5 mg/ml.

42. A tissue equivalent formed by the method of claim 35.

43. The tissue equivalent of claim 42, wherein the collagen and the fibrin are each at a concentration of from about 3 to about 30 mg/cm$^3$.

44. The tissue equivalent of claim 42, wherein the collagen is at a concentration of from about 10 to about 15 mg/cm$^3$ and the fibrin is at a concentration of from about 15 to about 25 mg/cm$^3$.

45. A method of joining a tear in the tissue equivalent of claim 1, the method comprising:
   (a) applying a mixture comprising fibrinogen and an agent which causes the formation of fibrin from fibrinogen to the tear; and (b) maintaining the tissue equivalent of step (a) under conditions to permit formation of fibrin.

46. A method of repairing a defect in a tissue equivalent comprising a hydrated collagen lattice contracted by a contractile agent or (i) a hydrated collagen lattice contracted by a contractile agent and (ii) fibrin, the method comprising:
(a) applying a mixture comprising fibrinogen and an agent which causes the formation of fibrin from fibrinogen to the defect in the tissue equivalent; and
(b) maintaining the tissue equivalent of step (a) under conditions to permit formation of fibrin.

* * * * *